(12) United States Patent
Cobelli et al.

(10) Patent No.: US 12,226,234 B2
(45) Date of Patent: Feb. 18, 2025

(54) RETROSPECTIVE RETROFITTING METHOD TO GENERATE A CONTINUOUS GLUCOSE CONCENTRATION PROFILE BY EXPLOITING CONTINUOUS GLUCOSE MONITORING SENSOR DATA AND BLOOD GLUCOSE MEASUREMENTS

(71) Applicant: Dexcom, Inc., San Diego, CA (US)

(72) Inventors: Claudio Cobelli, Padua (IT); Simone Del Favero, Padua (IT); Andrea Facchinetti, Trissino (IT); Giovanni Sparacino, Padua (IT)

(73) Assignee: Dexcom, Inc., San Diego, CA (US)

( * ) Notice: Subject to any disclaimer, the term of this patent is extended or adjusted under 35 U.S.C. 154(b) by 7 days.

(21) Appl. No.: 18/182,444

(22) Filed: Mar. 13, 2023

(65) Prior Publication Data
US 2023/0210412 A1     Jul. 6, 2023

Related U.S. Application Data

(63) Continuation of application No. 16/373,454, filed on Apr. 2, 2019, now Pat. No. 11,633,156, which is a
(Continued)

(51) Int. Cl.
*A61B 5/145*  (2006.01)
*A61B 5/00*   (2006.01)
(Continued)

(52) U.S. Cl.
CPC .......... *A61B 5/7207* (2013.01); *A61B 5/1451* (2013.01); *A61B 5/14532* (2013.01);
(Continued)

(58) Field of Classification Search
CPC . A61B 5/14503; A61B 5/1473; A61B 5/1486; A61B 5/14865; A61B 5/1451; A61B 2560/063
See application file for complete search history.

(56) References Cited

U.S. PATENT DOCUMENTS 10,299,733 B2     5/2019  Cobelli et al.
2002/0161288 A1*  10/2002 Shin .................... A61B 5/14865
                                              600/347
(Continued)

FOREIGN PATENT DOCUMENTS

WO     2011051922 A2     5/2011

OTHER PUBLICATIONS

Guerra S, Facchinetti A, Sparacino G, Nicolao GD, Cobelli C. Enhancing the accuracy of subcutaneous glucose sensors: a real-time deconvolution-based approach. IEEE Trans Biomed Eng. Jun. 2012;59(6): 1658-69. doi: 10.1109/TBME.2012.2191782. Epub Mar. 23, 2012. PMID: 22481799. (Year: 2012).*

(Continued)

*Primary Examiner* — Eric J Messersmith
(74) *Attorney, Agent, or Firm* — Patterson + Sheridan, LLP

(57) ABSTRACT

Continuous Glucose Monitoring (CGM) devices provide glucose concentration measurements in the subcutaneous tissue with limited accuracy and precision. Therefore, CGM readings cannot be incorporated in a straightforward manner in outcome metrics of clinical trials e.g. aimed to assess new glycemic-regulation therapies. To define those outcome metrics, frequent Blood Glucose (BG) reference measurements are still needed, with consequent relevant difficulties in outpatient settings. Here we propose a "retrofitting" algorithm that produces a quasi continuous time BG profile by simultaneously exploiting the high accuracy of available BG references (possibly very sparsely collected) and the high temporal resolution of CGM data (usually noisy and affected by significant bias). The inputs of the algorithm are: a CGM time series; some reference BG measurements; a model of blood to interstitial glucose kinetics; and a model of the deterioration in time of sensor accuracy, together with (if (Continued)

available) a priori information (e.g. probabilistic distribution) on the parameters of the model. The algorithm first checks for the presence of possible artifacts or outliers on both CGM datastream and BG references, and then rescales the CGM time series by exploiting a retrospective calibration approach based on a regularized deconvolution method subject to the constraint of returning a profile laying within the confidence interval of the reference BG measurements. As output, the retrofitting algorithm produces an improved "retrofitted" quasi-continuous glucose concentration signal that is better (in terms of both accuracy and precision) than the CGM trace originally measured by the sensor. In clinical trials, the so-obtained retrofitted traces can be used to calculate solid outcome measures, avoiding the need of increasing the data collection burden at the patient level.

24 Claims, 9 Drawing Sheets

Related U.S. Application Data continuation of application No. 14/770,803, filed as application No. PCT/IB2014/059121 on Feb. 20, 2014, now Pat. No. 10,299,733.

(60) Provisional application No. 61/767,032, filed on Feb. 20, 2013.

(51) Int. Cl.
*A61B 5/1495* (2006.01)
*G16H 10/40* (2018.01)
*G16H 50/20* (2018.01)
*G16H 50/30* (2018.01)

(52) U.S. Cl.
CPC .......... *A61B 5/1495* (2013.01); *A61B 5/7203* (2013.01); *A61B 5/7264* (2013.01); *A61B 5/7275* (2013.01); *A61B 5/7289* (2013.01); *G16H 10/40* (2018.01); *G16H 50/20* (2018.01); *G16H 50/30* (2018.01)

(56) References Cited

U.S. PATENT DOCUMENTS

| 2003/0060692 | A1 | 3/2003 | Ruchti et al. | |
|---|---|---|---|---|
| 2007/0173761 | A1 | 7/2007 | Kanderian, Jr. et al. | |
| 2008/0033254 | A1* | 2/2008 | Kamath | A61B 5/725 600/300 |
| 2008/0314395 | A1 | 12/2008 | Kovatchev et al. | |
| 2010/0280782 | A1* | 11/2010 | Harper | A61B 5/1473 702/104 |
| 2012/0215087 | A1* | 8/2012 | Cobelli | G16Z 99/00 600/365 |
| 2012/0262298 | A1 | 10/2012 | Bohm et al. | |
| 2013/0231543 | A1 | 9/2013 | Facchinetti et al. | |
| 2014/0182350 | A1 | 7/2014 | Bhavaraju et al. | |
| 2016/0073964 | A1 | 3/2016 | Cobelli et al. | |
| 2019/0223807 | A1 | 7/2019 | Cobelli et al. | |

OTHER PUBLICATIONS

A. Facchinetti, G. Sparacino and C. Cobelli, "Online Denoising Method to Handle Intraindividual Variability of Signal-to-Noise Ratio in Continuous Glucose Monitoring," in IEEE Transactions on Biomedical Engineering, vol. 58, No. 9, pp. 2664-2671, Sep. 2011, doi: 10.1109/TBME.2011.2161083. (Year: 2011).*
Barcelo-Rico et al., "A Multiple Local Models Approach to Accuracy Improvement in Continuous Glucose monitoring," Diabetes Techno! Ther, 2012, vol. 14(7), pp. 74-82.
Facchinetti A., et al., "An Online Self-Tunable Method to Denoise CGM Sensor Data," IEEE Transactions on Biomedical engineering, vol. 57 (3), Mar. 1, 2010, pp. 634-641.
Facchinetti A., et al., "Online Denoising Method to Handle Intra-Individual Variability of Signal-to-Noise Ratio in Continuous Glucose Monitoring," IEEE Trans Biomed Eng (BME), vol. 58(9), 2011, pp. 2664-2671.
Guerra S., et al., "Enhancing the Accuracy of Subcutaneous Glucose Sensors: A Real-Time Deconvolution-Based Approach," IEEE Transactions on Biomedical Engineering, vol. 59(6), Jun. 2012, pp. 1658-1669.
International Preliminary Search Report for Application No. PCT/IB2014/059121 dated Sep. 3, 2015 8pages.
International Search Report and Written Opinion for Application No. PCT/IB2014/059121 dated Jul. 18, 2014, 10 pages.
Leal Y., et al., "Real-Time Glucose Estimation Algorithm for Continuous Glucose Monitoring Using Autoregressive Models," Journal of Diabetes Science and Technology, vol. 4(2), Mar. 2010, pp. 391-403.
Palerm et al., "Hypoglycemia Prediction and Detection Using Optimal Estimation", Diabetes Technol Ther, 2005, vol. 7(1), pp. 3-14.

* cited by examiner

RETROSPECTIVE RETROFITTING METHOD TO GENERATE A CONTINUOUS GLUCOSE CONCENTRATION PROFILE BY EXPLOITING CONTINUOUS GLUCOSE MONITORING SENSOR DATA AND BLOOD GLUCOSE MEASUREMENTS

CROSS-REFERENCE TO RELATED APPLICATIONS

This application is a continuation of U.S. Non-Provisional application Ser. No. 16/373,454, filed Apr. 2, 2019, which is a continuation of U.S. Non-Provisional application Ser. No. 14/770,803, filed Aug. 26, 2015, now U.S. Pat. No. 10,299,733, which is the National Phase of International Patent Application No. PCT/IB2014/059121, filed Feb. 20, 2014, which claims benefit of and priority to U.S. Provisional Application No. 61/767,032, filed Feb. 20, 2013.

BACKGROUND

The present invention relates to continuous glucose monitoring (CGM) and, more specifically, to a retrospective "retrofitting" algorithm to improve accuracy and precision of glucose concentration levels by exploiting available reference glucose measurements in the blood and a new constrained regularized deconvolution method. The inputs of the retrofitting algorithm are: a CGM time series; some reference blood glucose (BG) measurements; a model of blood to interstitial glucose kinetics; and a model of the deterioration in time of sensor accuracy. The outputs are: an improved ("retrofitted") quasi-continuous glucose concentration signal that is better (in terms of both accuracy and precision) than the CGM trace originally measured by the sensor, together with its confidence interval; a retrospectively calibrated CGM time series; and a set of CGM and BG reference data that are discarded from the analysis because they are labeled as unreliable data or outliers.

DETAILED DESCRIPTION

Diabetes is a disease that causes abnormal glycemic values due to the inability of the pancreas to produce insulin (Type I diabetes) or to the inefficiency of insulin secretion and action (Type 2 diabetes). Patients affected by diabetes need to monitor their blood glucose (BG) level all day in order to control it and take countermeasures to keep it inside the normal range of 70-180 mg/dl as much as possible. Diabetic patients are forced to take exogenous insulin infusions or drugs, whose scheduling and dosages are calculated on the basis of BG measurements.

According to the current gold standard, BG measurements can be collected in two main ways: i) during daily life by means of capillary finger-pricks, i.e. self monitoring blood glucose (SMBG) 4-5 times per day at most; ii) during hospitalized clinical trials, by means of gold standard laboratory instruments. Both these BG monitoring systems are reasonably accurate. However, sampling in the blood can be done only sporadically, and, as a result, fast fluctuations of the patient's glucose concentrations can result invisible. FIG. 1 shows a conceptual simulated example where the sparseness of SMBG measurements (triangles) does not allow to fully capture glucose variations evident in the continuous-time glycemic profile (dashed line) and even impair the detection of some hypo/hyperglycemic events (e.g. around times 10 and 30).

In the last 15 years, continuous glucose monitoring (CGM) sensors have been introduced. Differently from BG measurement systems, these devices measure glucose in the interstitial fluid rather than in the circulation, reducing the invasiveness and allowing the visualization of real-time glucose values every 1-5 minutes for several consecutive days. CGM sensors provide a more comprehensive picture of glucose fluctuations, evidencing critical episodes that could be undetectable using SMBG systems. However, CGM devices still suffer for some inaccuracy. In fact, when compared to BG references provided by SMBG or laboratory devices, CGM profiles sometimes present transient or systematic under/overestimations, outlier samples and portions of missing data. FIG. 2 shows a conceptual example where a representative CGM time series (dots) is compared to the same SMBG references (triangles) and true simulated glycemia (dashed line) already presented in FIG. 1. A 1st order interpolation of CGM values (dots) is reported to facilitate visual comparison. CGM has a much higher temporal resolution (5 min sampling) than SMBG, but sometimes exhibits systematic under/overestimations of the true concentration. Differently from SMBG references, CGM allows a fair assessment of glucose fluctuations. However, systematic overestimation of CGM is visible from hour 20 to 30, together with a transient underestimation at time 12. Obviously, lack of accuracy of CGM is detrimental to its clinical use and, at present time, is recognized in the research community as a bottleneck for several practical applications.

In this document we describe a retrospective retrofitting procedure that creates a quasi-continuous glucose concentration signal, which is better, in terms of both accuracy and precision, than the CGM trace originally measured by the CGM sensor. This is done by exploiting few, sparse but accurate, BG reference samples (that could be either SMBGs or BG values obtained via laboratory instruments) and frequent quasi-continuous CGM data, which can be noisy and biased. The procedure incorporates an original constrained-deconvolution approach and returns in output a quasi-continuous glucose concentration profile, hereafter referred as the retrofitted glucose concentration time-series, which tackles in great part the accuracy and precision issues of the original CGM sensor data.

Some methods to increase accuracy and precision of CGM time series are available.

i) The first class of methods aims at improving online the precision of CGM output by reducing the effect of measurement noise. The method proposed by Palerm and Bequette (Diabetes Technol Ther 2005) is based on a Kalman filter with fixed parameters. The methods of Facchinetti et al. (IEEE Trans Biomed Eng 2010 and 2011), in particular, exploit a Bayesian approach to denoise CGM data taking into account interindividual and intraindividual variability of the signal-to-noise ratio. These methods do not take into account any physiological/technological model to compensate for possible lack of accuracy.

ii) The second class of methods is aimed to improve accuracy of CGM data in real time. In a first approach, employed by Knobbe and Buckingham (Diabetes Technol Ther 2005) and Facchinetti et al. (Diabetes Technol Ther 2010), a state-space Bayesian framework exploiting a priori knowledge on the variability of the sensitivity of CGM sensor and a model of the blood-to-interstitium glucose kinetics was adopted and implemented via extended Kalman filtering. In a second approach, used in Guerra et al. (IEEE Trans Biomed Eng 2012), CGM data were enhanced by using a deconvolution-based method relying on a physiological model of the blood to interstitial fluid glucose kinetics. In a third approach, a raw deconvolution is used to improve CGM data accuracy (Kovatchev B. and King C., U.S. Patent Appl. 2008/0314395 A1, Dec. 25, 2008). Other approaches are based e.g. on multiple local models (Barcelo-Rico et al., Diabetes Technol Ther 2012), on autoregressive models (Leal et al., J Diabetes Sci Technol 2010), fixed-delay models and FIR filters (Kanderian S. and Steil G. M., U.S. Patent 2007/0173761 A1, Jul. 26, 2007).

The methods under i) address the problem of precision of CGM data, but not that of the possible lack/loss of accuracy. The methods under ii) consider the problem of possible lack of accuracy, but not that of lack of precision. In addition, in order to work online, the methods of the second class are fed with average/population parameters, which could make them suboptimal. Furthermore, all the methods above described (both under i) and ii)) are causal and are thus unable to take into account also future data, a possibility that should be usefully exploited in a retrospective analysis setting.

SUMMARY OF THE INVENTION

The "retrofitting" method that we describe here is able to improve both precision and accuracy of CGM data simultaneously. An additional key feature is that it is conceived to work retrospectively, so that all information collected during the monitoring, consisting in CGM values and BG reference measurements, can be used. Finally, all the parameters employed in the "retrofitting" algorithm, e.g. the parameters of the calibration law and the time-constant of the model used to describe the plasma-to-interstitial fluid glucose kinetics, are optimized on patient data, so that possible sub-optimality of real-time approaches is avoided.

The invention employs an algorithm, hereafter named as retrofitting procedure, which receives in input (as shown in FIG. 3, left): a continuous glucose monitoring (CGM) time series; some reference blood glucose (BG) measurements together with their confidence interval; other relevant inputs that could help in describing fluctuations in glucose dynamics, such as meals quantity and scheduling, hypo treatments, drugs, physical activity and stress information; a model of blood-to-interstitial glucose kinetics; a model of CGM sensor drift-in-time/degradation of accuracy, together with a priori information (e.g. probabilistic distribution) on the parameters of the model; other relevant models that could help in describing fluctuations in glucose dynamics, such as those for meal absorption, insulin action, etc. The algorithm first checks for the presence of possible artifacts or outliers on both CGM and BG data, and then rescales the CGM time series exploiting a retrospective calibration technique based on regularized deconvolution approach subject to the constraint that the deconvoluted profile should stay within the confidence interval of the BG references. A shown in FIG. 3, the retrofitting procedure produces, as output: an improved "retrofitted" quasi-continuous glucose concentration signal that is better (in terms of both accuracy and precision) than the CGM trace originally measured by the sensor, together with its confidence interval; a retrospectively calibrated CGM time series; and a set of CGM and BG references data that are discarded from the analysis because labeled as unreliable data or outliers. The retrofitted quasi-continuous glucose concentration signal can be interpreted as an estimation of the BG profile of the patient occurred during the monitoring.

As schematized in FIG. 3, the retrofitting procedure is based on three main steps (labelled as sub-blocks A, B and C in the figure):

Data preprocessing and outlier detection. Aimed to detect unreliable data and outliers. This first preprocessing block receives in input CGM and BG time series. Outliers and unreliable data are isolated and excluded from the following steps of the analysis. The outputs are: discarded BG, discarded CGM, preprocessed BG, and preprocessed CGM data.

Retrospective CGM calibration. Aimed to compensate for systematic under/overestimation of CGM time series with respect to reference BG values due to sensor drift, errors in CGM sensor calibration, changes in sensor sensitivity. A retrospective calibration of the CGM time series is performed. Retrospective calibration parameters are estimated exploiting a model of the blood-to-interstitial glucose kinetics and a model of sensor drift/degradation. The estimation procedure could be able to exploit, if available, a priori information (e.g. probabilistic distribution) on the parameters of the model (e.g. Bayesian estimation). The output of the second step is a retrospectively calibrated CGM time series, which is more accurate than the original CGM profile (e.g. closer to the reference BG data).

Constrained inverse problem solver. The recalibrated CGM is deconvoluted through a deconvolution module, which is also fed by a model of blood-to-interstitial glucose kinetics (together with, if available, a priori information on the parameters of the model), all BG reference measurements that have not been labeled as outliers in step 1, and a confidence interval on them. The output of this block is the retrofitted glucose concentration profile with its confidence interval. The deconvolution step allows: reducing delays/distortions due to glucose kinetics from blood to the interstitial fluid; determining a (quasi) continuous time estimate of the glucose profile into the blood by taking advantage of the available BG reference measurements (in particular, thanks to the inclusion of constraints within the deconvolution algorithm, the retrofitted glucose profile passes within the confidence interval of the available BG references); improving precision of the retrofitted glucose profile with respect to the originally measured CGM time-series (i.e. reduce uncertainty due to measurement noise) thanks to the exploitation of a physiological prior on the signal smoothness.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE DRAWINGS

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
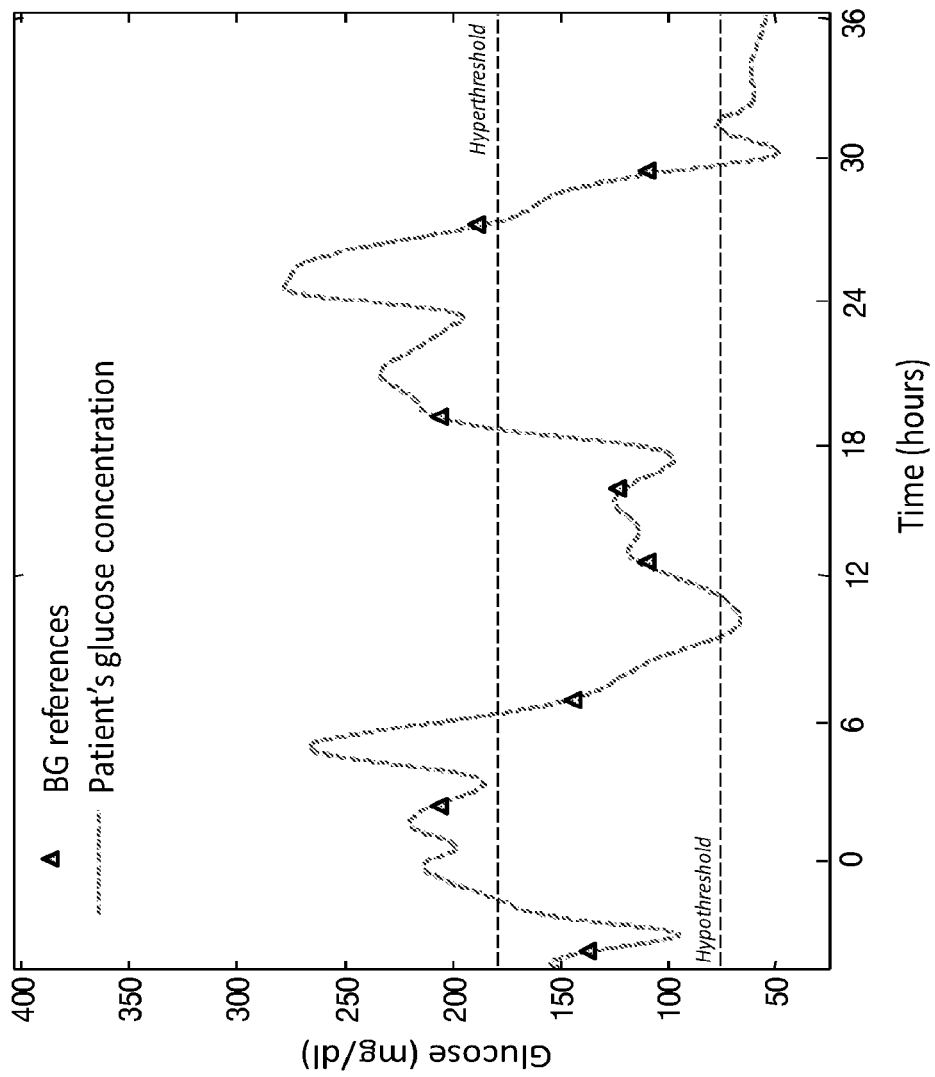
FIG. 1 is a graph showing SMBG measurements versus continuous-time glycemia.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Figure 3:
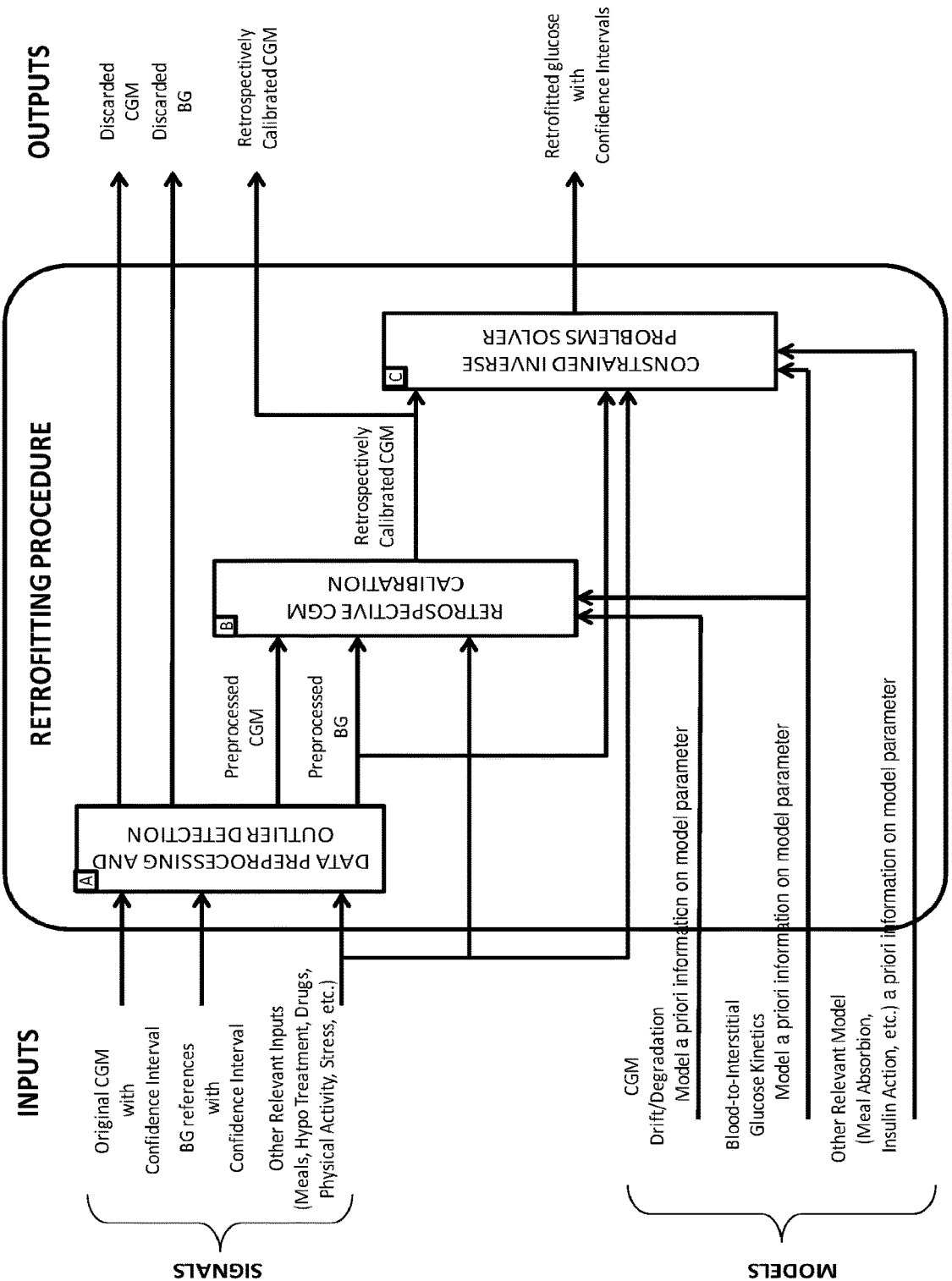
FIG. 3 is a block scheme representing how the retrofitting algorithm works.

FIG. 3 is a block scheme representing how the retrofitting algorithm works. On the right side, signals and models giving an input to the retrofitting algorithm as shown. In the middle section the core of the retrofitting procedure comprising three main sub-blocks is depicted: A data preprocessing and outlier detection, B. retrospective CGM calibration, and C. constrained inverse problem solver. On the left side these signals returned in output all shown. Starting from the schematization in sub-blocks of the retrofitting procedure depicted in FIG. 3, we present a possible and preferred embodiment.

Sub-Block A. Data Preprocessing and Outlier Detection.

The aim of this sub-block (sub-block A in FIG. 3) is to detect unreliable data and outliers. The block receives in input CGM and BG time series that will be used to create the retrofitting profile. The block contains an algorithm that is employed to detect outliers and/or unreliable values on both BG and CGM time series. An example of outlier is a single sample that is not consistent with the trends of the time series. An example of unreliable values is two, or more, consecutive values whose distance in time is not able to explain, from a physiological or technological point of view, their distance in glucose space. Outliers and anomalous data are identified and excluded from the successive steps of analysis. The outputs are: discarded BG, discarded CGM, preprocessed BG, and preprocessed CGM data.

Figure 4:
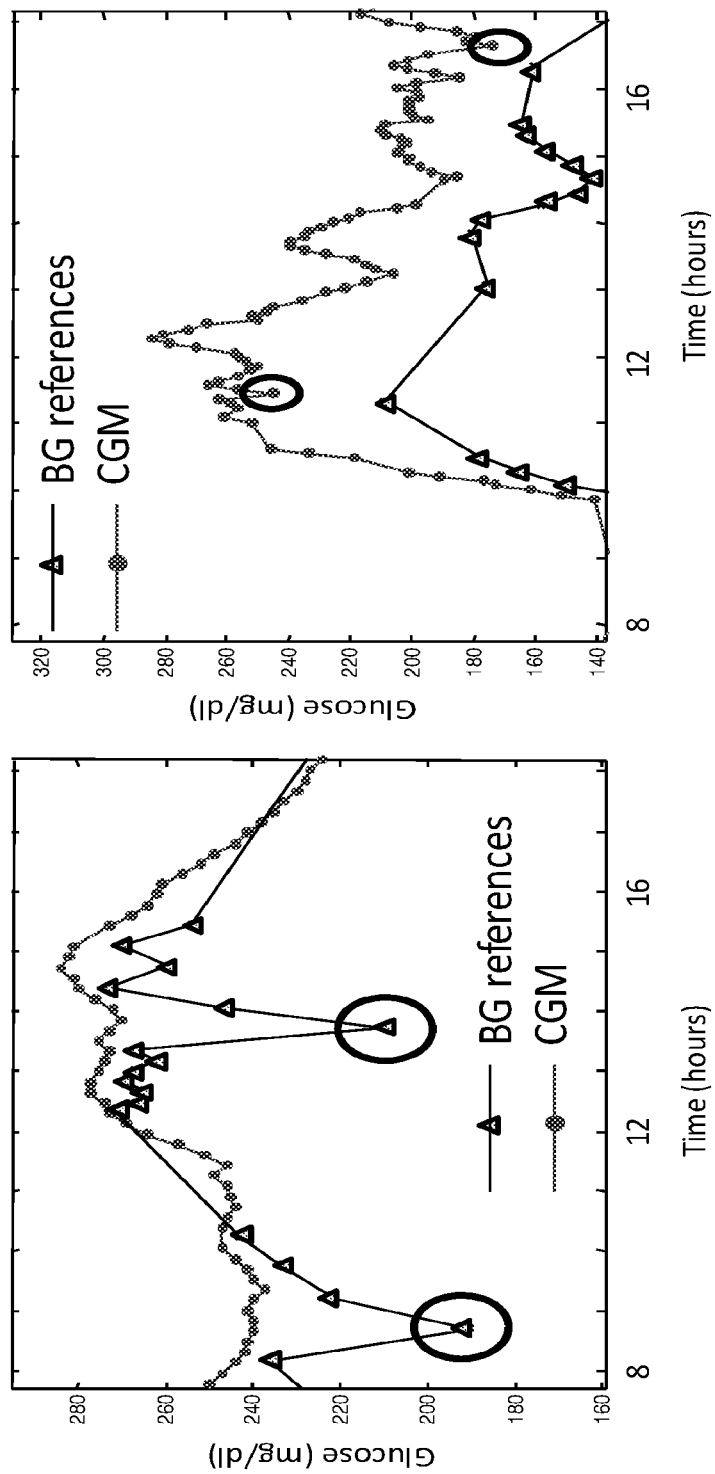
FIG. 4 includes two graphs showing examples of BG and CGM outliers or unreliable values.

A possible algorithm for this sub-block should calculate the first-order time derivative of the time series, using finite differences or any statistically-based estimation procedure (e.g. a Bayesian smoothing procedure). The time series of the first-order differences is inspected for the presence of outliers and unreliable values following a given criterion. For example, a possible criterion for the detection of outliers checks any couple of two consecutive derivatives. If both amplitudes are greater than a given threshold X and have opposite sign, then the value in the middle is labeled as outlier. As far as the detection of unreliable values is concerned, a possible criterion checks every couple of two consecutive values. Every couple of values that are taken Y minutes apart each other and whose distance in the glucose space is greater than Z mg/dl, where Z=g(Y), are labelled as unreliable. FIG. 4 shows examples of BG (triangles) and CGM (dots) outliers or unreliable values that are eliminated in this step. In the left diagram two BG unreliable values are circled. In the right diagram two CGM outliers are circled.

The detection of outliers or unreliable data can be improved also exploiting other relevant inputs that could help in describing fluctuations in glucose dynamics (e.g. meals quantity and scheduling, hypo treatments, drugs, physical activity and stress information, etc.) opportunely modeled by other relevant models (e.g. models for meal absorption, insulin action, etc.), when available.

Sub-Block B. Retrospective CGM Calibration.

The sub-block (sub-block B in FIG. 3) is aimed to compensate for systematic under/overestimation of CGM time series with respect to reference BG values due to e.g. drift in time, errors in CGM sensor calibration, and changes in sensor sensitivity. This is done by performing a retrospective calibration of the CGM time series. From the sub-block A previously described, the sub-block B receives in input the preprocessed BG and preprocessed CGM data and returns in output a retrospectively calibrated CGM profile which is more accurate (e.g. closer to the reference BG data) than the measured CGM one, since errors due to drifts, suboptimal calibration, etc. have been mitigated.

Figure 5:
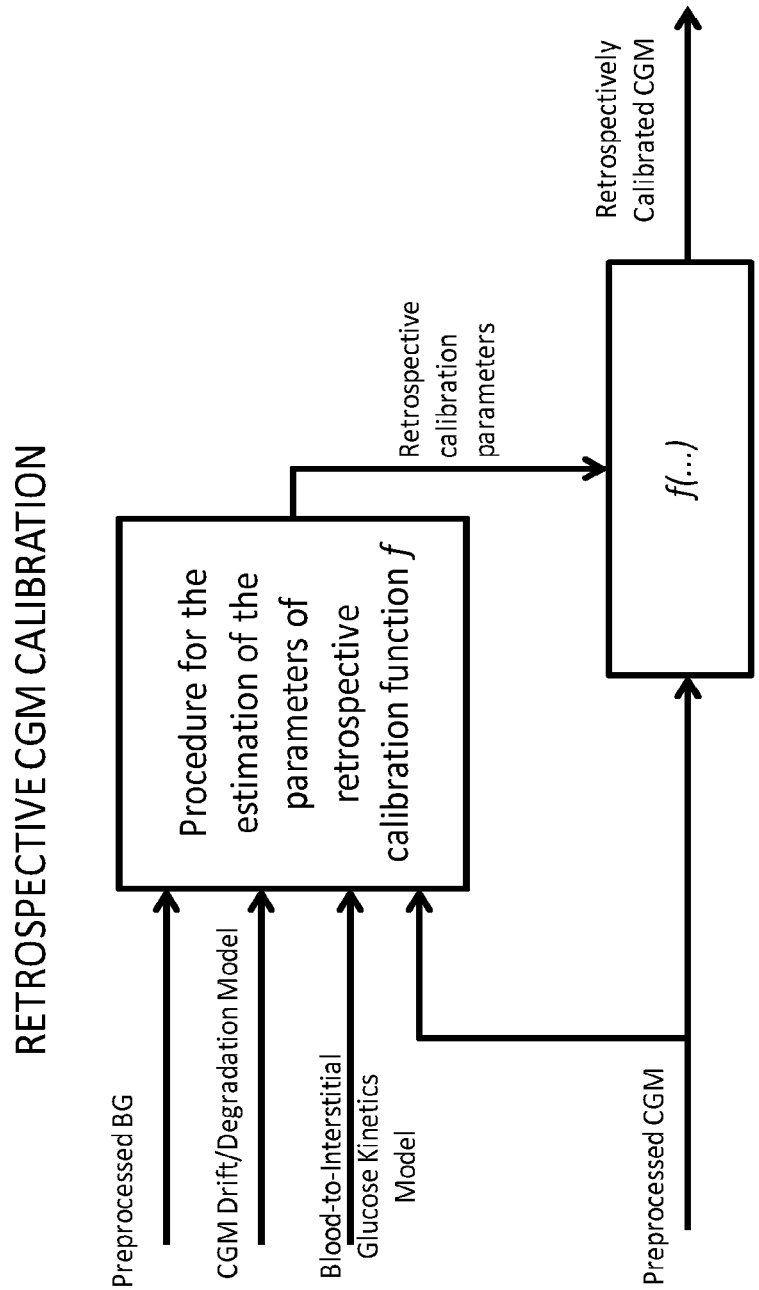
FIG. 5 is a block diagram depicting the retrospective CGM calibration procedure.
Figure 6:
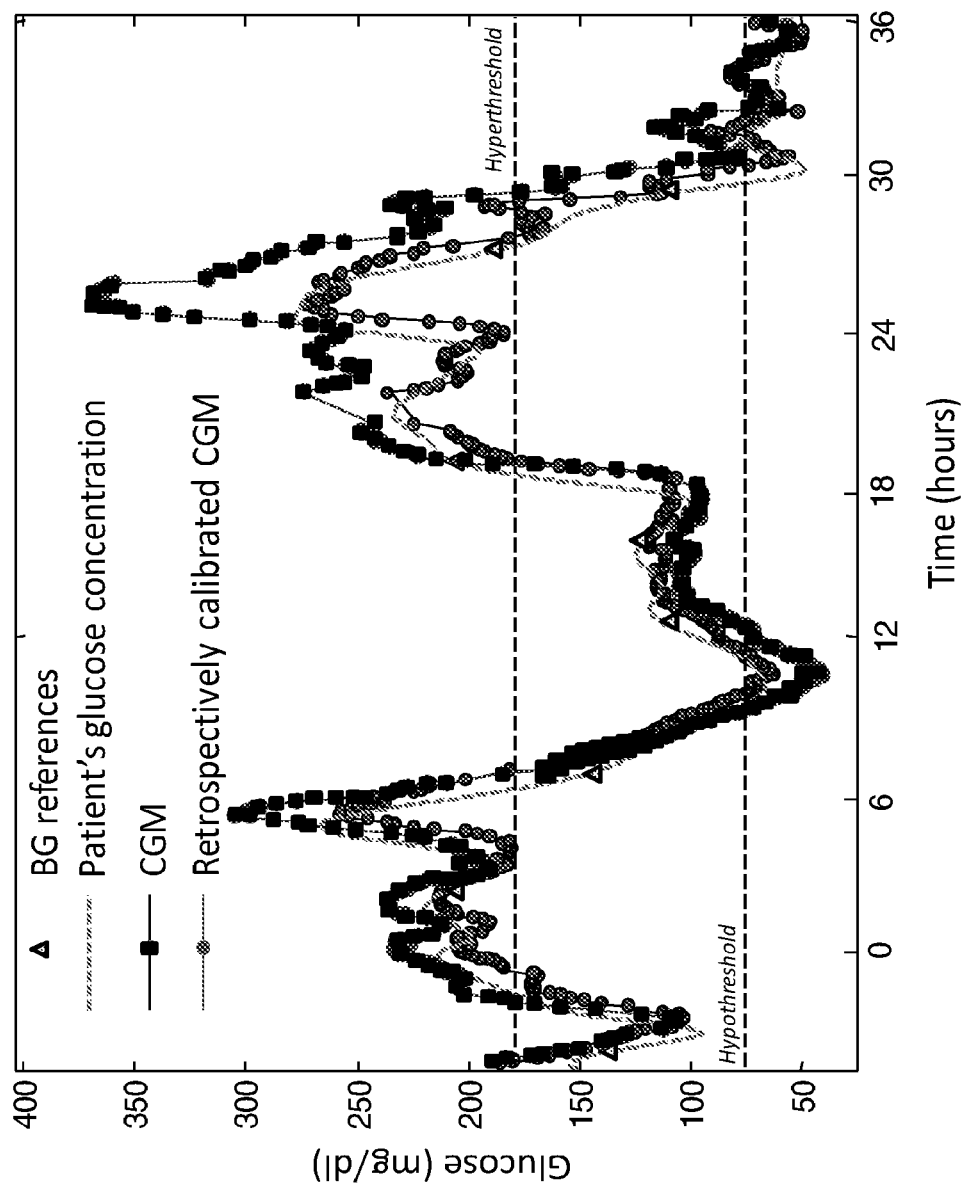
FIG. 6 is a graph showing an example of retrospectively calibrated CGM versus originally measured CGM time series.

A possible algorithm to perform the retrospective calibration divides the CGM time series history into several intervals using the times of calibration events as separators. The history of the available BG references is divided in the same temporal intervals. Under the assumption that calibration parameters remain the same between two consecutive calibrations and that the performance of the sensor degrades in time due to changes in the sensitivity of the sensor, each portion of CGM data is calibrated against all the BG references falling in the same temporal interval. The calibration rule is a regression law f that receives in input the preprocessed CGM time series and returns in output the retrospectively calibrated CGM time series. For example, f=f (a,b,c) where a is a gain parameter, b is an offset, and c is a parameter that takes into account the temporal trend of the data. The parameters of the regression law f are estimated from available data exploiting a model of the blood-to-interstitial fluid glucose transportation dynamics and a model for sensor drift/degradation. The estimation procedure could be able to exploit, if available, a priori information (e.g. probabilistic distribution) on the parameters of the model (e.g. Bayesian estimation). A schematization of the algorithm of sub-block B is reported in FIG. 5. An example of the retrospectively calibrated CGM time series given in output in this step is shown in FIG. 6, in which the retrospectively calibrated CGM is apparently closer (in terms of absolute error) to the reference BG measurements than the originally measured CGM. FIG. 6 shows the same data as in FIG. 1 and FIG. 2, and an example of retrospectively calibrated CGM (dots) vs originally measured CGM (squares) time series is depicted.

The retrospective CGM calibration can be improved also exploiting other relevant inputs that could help in describing fluctuations in glucose dynamics (e.g. meals quantity and scheduling, hypo treatments, drugs, physical activity and stress information, etc.) opportunely modeled by other relevant models (e.g. models for meal absorption, insulin action, etc.), when available. If available, a priori information (e.g. probabilistic distribution) on the parameters of the model can be provided.

Sub-Block C. Constrained Inverse Problem Solver.

The third sub-block of the retrofitting procedure (sub-block C in FIG. 3, middle) performs constrained deconvolution. The inputs of this sub-block are the retrospectively calibrated CGM data given in output by sub-block B, all the BG reference measurements that have not been labeled as outliers or unreliable values together with their confidence interval (e.g., the coefficient of variation or the standard deviation), given in output by sub-block A, and a model of blood-to-interstitium glucose kinetics, e.g. the two-compartment model presented by Rebrin et al. (Am J Physiol 1999). If available, a priori information (e.g. probabilistic distribution) on the parameters of the model can be provided. The block contains an algorithm that performs the constrained deconvolution of the retrospectively calibrated CGM profile, and allows estimating, at (quasi) continuous time the profile of glucose concentration in blood that should have generated that CGM profile. Deconvolution can be based on the regularization approach, see De Nicolao et al. (Automatica 1997). From a mathematical point of view, the deconvolution algorithm finds the solution to the following problem:

$$\hat{u} = \underset{\substack{u \\ BG-toll<u<BG+toll}}{\operatorname{argmin}} \left( (CGM_{retrocalibrated} - Gu)^T \sum_{v}^{-1} (CGM_{retrocalibrated} - Gu) + \gamma \cdot u^T(F^T F)u \right) \quad (1)$$

where $CGM_{retrocalibrated}$ is a N×1 vector containing samples of the retrospectively calibrated CGM profile produced by sub-block B, G is the N×N matrix obtained by discretizing the blood-to-interstitial fluid glucose kinetics model, $\Sigma_v^{-1}$ is the inverse of the CGM measurement error covariance N×N matrix, F is a N×N Toeplitz lower triangular matrix that acts as a discrete differentiator, BG is a N×1 vector containing all the BG values received in input, toll is the confidence interval on them, and û is the vector containing the samples of the retrofitted (quasi) continuous glucose concentration time series. In equation (1) it is clear that, for every BG reference value available, the retrofitted glucose concentration profile û should pass close to it, where close is defined by the confidence interval (toll) received in input (constraint). This step allows: eliminating delays/distortions due to glucose transportation from blood to the interstitial fluid by using regularized deconvolution; improving the estimate of the BG signal taking advantage of the BG reference measurements (thanks to the constraints, the retrofitted glucose profile lies within the confidence interval of the available BG references); exploiting a physiological prior on the smoothness of the BG profile to increase precision (i.e. reducing uncertainty due to measurement noise). An example of the output of the constrained deconvolution step, i.e. the retrofitting (quasi) continuous glucose time series, is showed in FIG. 7.

The constrained deconvolution can be improved also exploiting other relevant inputs that could help in describing fluctuations in glucose dynamics (e.g. meals quantity and scheduling, hypo treatments, drugs, physical activity and stress information, etc.) opportunely modeled by other relevant models (e.g. models for meal absorption, insulin action, etc.), when available. If available, a priori information (e.g. probabilistic distribution) on the parameters of the model can be provided.

Assessment of the Invention

The retrofitting procedure has been validated on 43 datasets of type 1 diabetic patients. For each patient at least 72 hours of CGM monitoring and frequent BG references were available. BG references have been divided into training-set references, used by the retrofitting algorithm, and test-set references, not used by the retrofitting algorithm and exploited to assess the accuracy of the retrofitted continuous glucose concentration profile.

Figure 2:
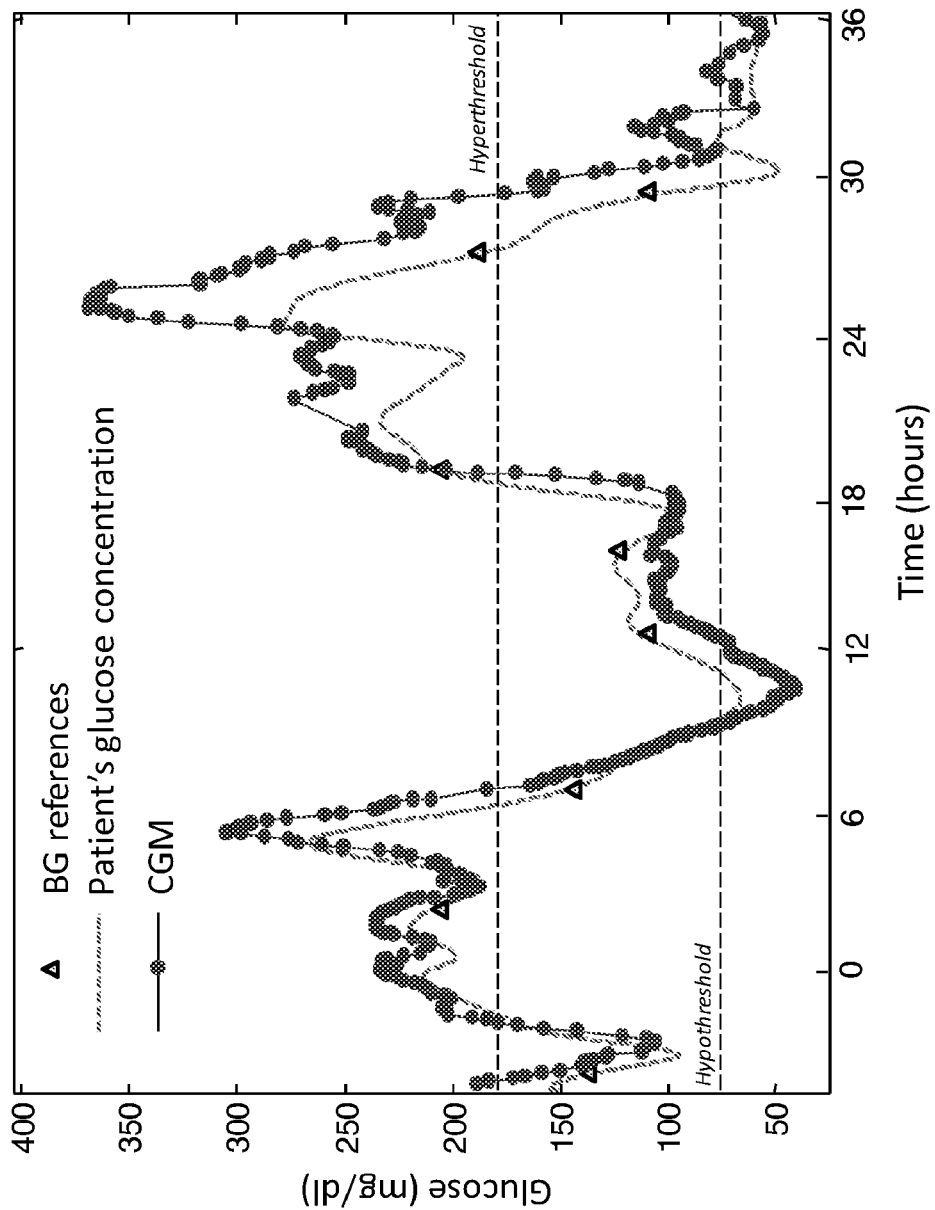
FIG. 2 is a graph showing a comparison of CGM time series (blue dots) vs SMBG.
Figure 7:
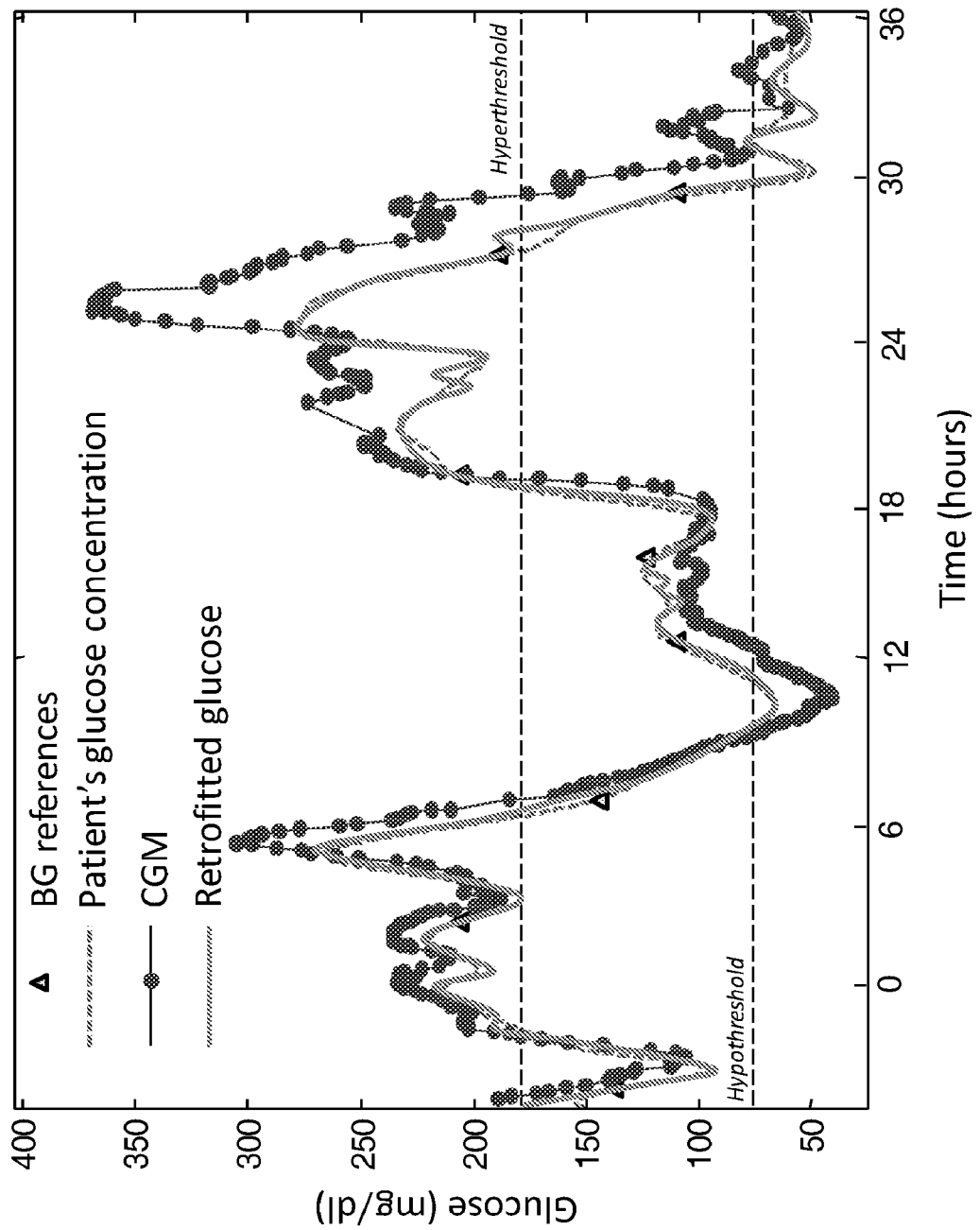
FIG. 7 is a graph showing retrofitted glucose concentration time series versus originally measured CGM time series.
Figure 8:
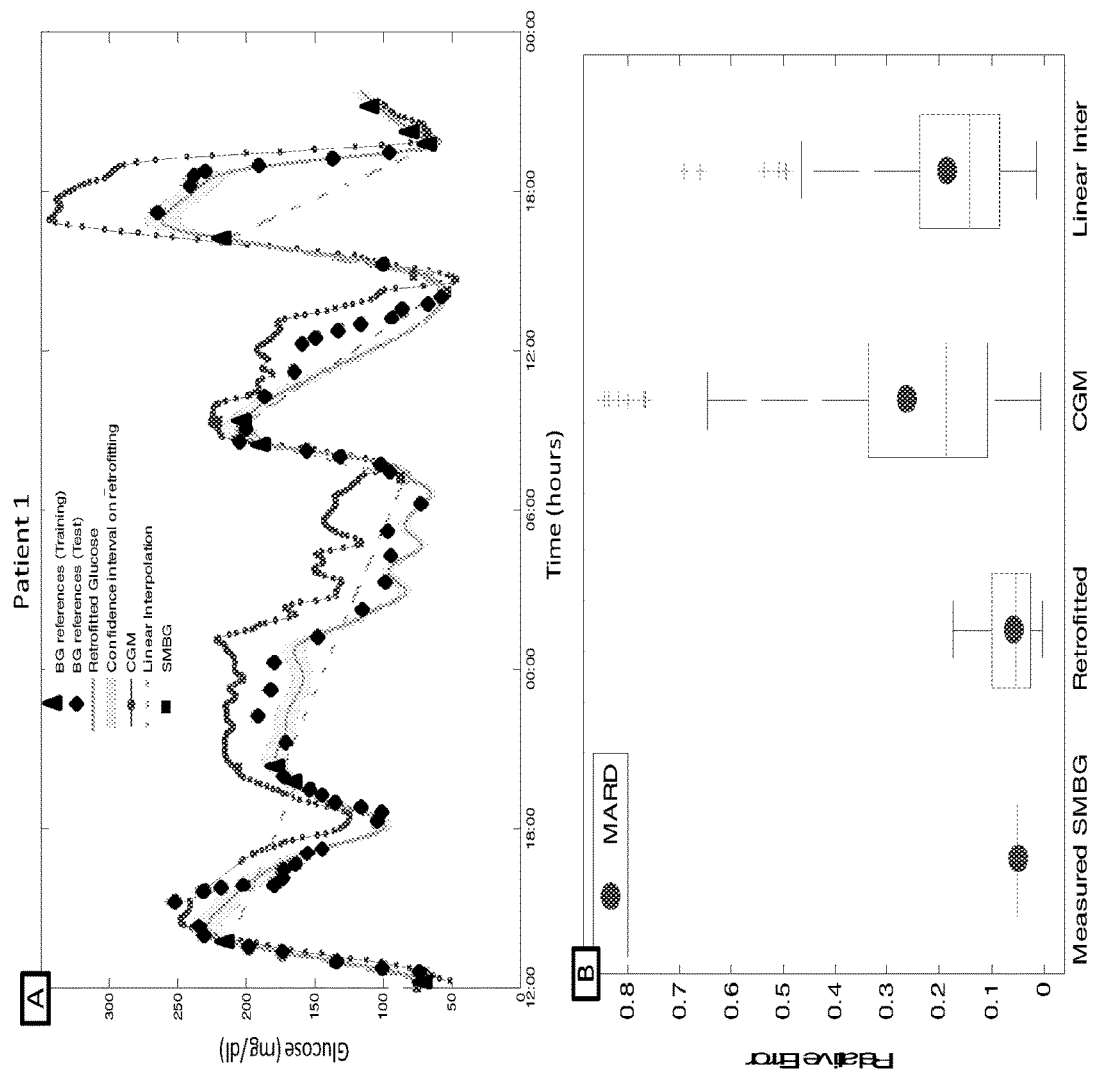
FIG. 8 includes two graphs showing results for a first patient.
Figure 9:
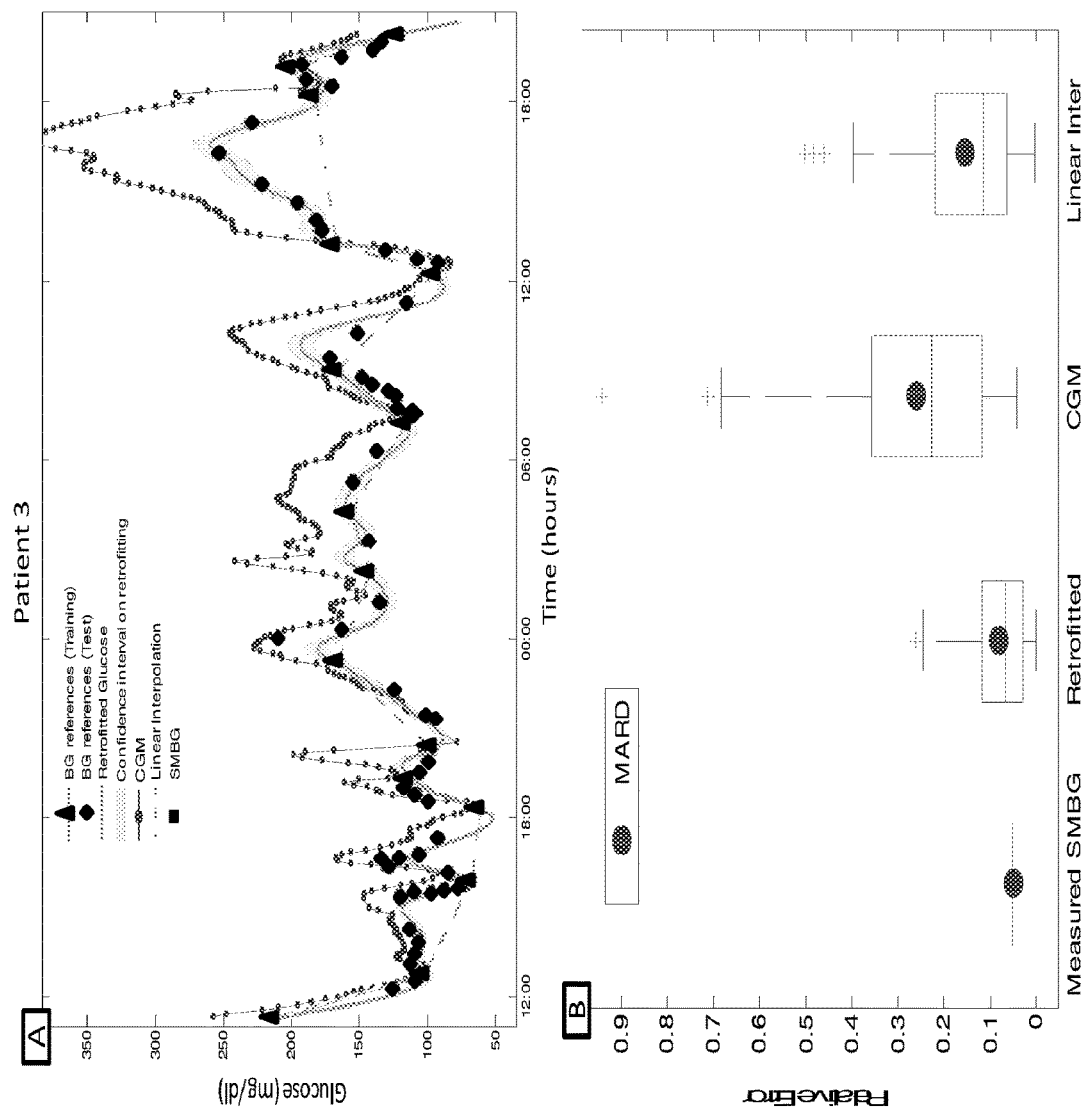
FIG. 9 includes two graphs showing results for a second patient.

FIG. 7 shows the same subject as FIGS. 1, 2, and 6. Retrofitted glucose concentration time series is shown by a line vs originally measured CGM time series shown in dots. FIGS. 8 and 9 (top) show the outcomes of the retrofitting technique in two representative subjects of the dataset (#1 and #3 respectively). CGM trace is depicted in dots, triangles are the BG measurements assigned to the training-set and therefore provided to the retrofitting method. The output of the retrofitting method is the continuous line (the grey area is its confidence interval) and has to be compared with the test BG references (diamonds, depicted with their confidence intervals). By eye inspection, it is evident the improvement in accuracy with respect to CGM or a simple linear interpolation of BG references (dashed line), and also the improvement of smoothness with respect to CGM.

FIGS. 8 and 9 (bottom) show, for each of the representative patients, a boxplot of the relative errors on test-set. The profile obtained by the retrofitting algorithm is compared with the original CGM values and with linear interpolation of the training-set references. Nominal finger-stick accuracy is also reported for comparison. For both patients, the relative error is significantly reduced with respect to CGM and linear interpolation, resulting in about a 3-fold reduction of the MARD (mean absolute relative deviation), now comparable with that of finger-stick measurements, and a similar reduction of both the 90th and 75th percentiles of error distributions.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A method of generating a glucose concentration profile for a user, comprising:
   receiving continuous glucose monitoring (CGM) time series data and reference blood glucose data, wherein the reference blood glucose data comprises glucose data from a user-taken sample;
   processing the CGM time series data and reference blood glucose data to detect unreliable data;
   discarding the detected unreliable data from the CGM time series data and reference blood glucose data to obtain a second CGM time series data and a second reference blood glucose data;
   calibrating the second CGM time series data retrospectively based on the second reference blood glucose data to generate a retrospectively calibrated CGM signal;
   rescaling the retrospectively calibrated CGM signal to stay within a confidence interval of the second reference blood glucose data; and
   generating a retrofitted glucose concentration profile based on the retrospectively calibrated CGM signal.

2. The method of claim 1, wherein detecting the unreliable data is based on additional inputs selected from a group consisting of data regarding meals consumed, data regarding treatment taken for hypoglycemia, data regarding drugs taken, data regarding physical activity, and data regarding stress.

3. The method of claim 1, wherein the confidence interval is a coefficient of variation or a standard deviation from the second reference blood glucose data.

4. The method of claim 1, wherein the glucose data from the user-taken sample comprises glucose data collected from a finger-prick or from a laboratory measurement.

5. The method of claim 1, wherein generating the retrospectively calibrated CGM signal compensates for systematic underestimation and overestimation of CGM time series with respect to reference blood glucose data due to one or more of blood-to-interstitial glucose kinetics, sensor drift, errors in CGM sensor calibration, and changes in sensor sensitivity.

6. The method of claim 1, wherein generating the retrofitted glucose concentration profile comprises performing constrained deconvolution of the retrospectively calibrated CGM signal.

7. The method of claim 6, wherein performing constrained deconvolution is based on a blood-to-interstitial glucose kinetics model.

8. The method of claim 1, further comprising:
displaying, on a user interface, a retrofitted glucose concentration profile.

9. A system for generating a glucose concentration profile for a user, comprising:
at least one memory storing instructions;
at least one processor configured to execute the instructions to:
receive continuous glucose monitoring (CGM) time series data and reference blood glucose data, wherein the reference blood glucose data comprises glucose data from a user-taken sample;
process the CGM time series data and reference blood glucose data to detect unreliable data;
discard the detected unreliable data from the CGM time series data and reference blood glucose data to obtain a second CGM time series data and a second reference blood glucose data;
calibrate the second CGM time series data retrospectively based on the second reference blood glucose data to generate a retrospectively calibrated CGM signal;
rescale the retrospectively calibrated CGM signal to stay within a confidence interval of the second reference blood glucose data; and
generate a retrofitted glucose concentration profile based on the retrospectively calibrated CGM signal.

10. The system of claim 9, wherein the detection of the unreliable data is based on additional inputs selected from a group consisting of data regarding meals consumed, data regarding treatment taken for hypoglycemia, data regarding drugs taken, data regarding physical activity, and data regarding stress.

11. The system of claim 9, wherein the confidence interval is a coefficient of variation or a standard deviation from the second reference blood glucose data.

12. The system of claim 9, wherein the glucose data from the user-taken sample comprises glucose data collected from a finger-prick or from a laboratory measurement.

13. The system of claim 9, wherein the generation of the retrospectively calibrated CGM signal compensates for systematic underestimation and overestimation of CGM time series with respect to reference blood glucose data due to one or more of blood-to-interstitial glucose kinetics, sensor drift, errors in CGM sensor calibration, and changes in sensor sensitivity.

14. The system of claim 9, wherein the generation of the retrofitted glucose concentration profile comprises performing constrained deconvolution of the retrospectively calibrated CGM signal.

15. The system of claim 14, wherein performing constrained deconvolution is based on a blood-to-interstitial glucose kinetics model.

16. The system of claim 9, wherein the processor is further configured to execute instructions to:
display, on a user interface, a retrofitted glucose concentration profile.

17. A non-transitory computer-readable storage medium storing instructions, that when executed by one or more processors, cause the one or more processors to perform a method for generating a glucose concentration profile for a user, the method comprising:
receiving continuous glucose monitoring (CGM) time series data and reference blood glucose data, wherein the reference blood glucose data comprises glucose data from a user-taken sample;
processing the CGM time series data and reference blood glucose data to detect unreliable data;
discarding the detected unreliable data from the CGM time series data and reference blood glucose data to obtain a second CGM time series data and a second reference blood glucose data;
calibrating the second CGM time series data retrospectively based on the second reference blood glucose data to generate a retrospectively calibrated CGM signal;
rescaling the retrospectively calibrated CGM signal to stay within a confidence interval of the second reference blood glucose data; and
generating a retrofitted glucose concentration profile based on the retrospectively calibrated CGM signal.

18. The non-transitory computer-readable storage medium of claim 17, wherein detecting the unreliable data is based on additional inputs selected from a group consisting of data regarding meals consumed, data regarding treatment taken for hypoglycemia, data regarding drugs taken, data regarding physical activity, and data regarding stress.

19. The non-transitory computer-readable storage medium of claim 17, wherein the confidence interval is a coefficient of variation or a standard deviation from the second reference blood glucose data.

20. The non-transitory computer-readable storage medium of claim 17, wherein the glucose data from the user-taken sample comprises glucose data collected from a finger-prick or from a laboratory measurement.

21. The non-transitory computer-readable storage medium of claim 17, wherein generating the retrospectively calibrated CGM signal compensates for systematic underestimation and overestimation of CGM time series with respect to reference blood glucose data due to one or more of blood-to-interstitial glucose kinetics, sensor drift, errors in CGM sensor calibration, and changes in sensor sensitivity.

22. The non-transitory computer-readable storage medium of claim 17, wherein generating the retrofitted glucose concentration profile comprises performing constrained deconvolution of the retrospectively calibrated CGM signal.

23. The non-transitory computer-readable storage medium of claim 22, wherein performing constrained deconvolution is based on a blood-to-interstitial glucose kinetics model.

24. The non-transitory computer-readable storage medium of claim 17, further comprising:
 displaying, on a user interface, a retrofitted glucose concentration profile.

* * * * *